United States Patent [19]

Durzan et al.

[11] Patent Number: 5,547,866

[45] Date of Patent: Aug. 20, 1996

[54] TAXANE PRODUCTION IN HAPLOID-DERIVED CELL CULTURES

[75] Inventors: Don J. Durzan; Frank F. Ventimiglia, both of Davis, Calif.

[73] Assignee: The Regents of the University of California, Oakland, Calif.

[21] Appl. No.: 277,463

[22] Filed: Jul. 20, 1994

[51] Int. Cl.⁶ .............................. C12P 17/02; C12P 1/00
[52] U.S. Cl. .................. 435/123; 435/41; 435/240.4; 435/240.46; 435/240.48; 549/510
[58] Field of Search ..................... 435/123, 41, 240.4, 435/240.46, 240.48; 549/510

[56] References Cited

U.S. PATENT DOCUMENTS 5,019,504  5/1991  Christen .

FOREIGN PATENT DOCUMENTS

WO92/13961  8/1992  WIPO .

OTHER PUBLICATIONS

Zenkteler, M.A., et al. (1970) "Cytological studies on the regenerating mature female gametophyte of *Taxus baccata* L. and mature endosperm of *Tilia platyphyllos* Scop. in vitro culture", *Acta Sacietatis Botanicorum Poloniae*, 1:161–173.

Gibson, D. M., et al. (1993) "Initiation and growth of cell lines of *Taxus brevifolia* (Pacific yew)", *Plant Cell Reports*, 12:479–482.

Fett–Neto, Arthur G., et al. (1993) "Improved Growth and Taxol Yield in Developing Calli of *Taxus cuspidata* by Medium Composition Modification", *Bio/Technology*, 11:731–734.

Rohr, Rene (1982) "Activation et proliferation des cellules du megagametophyte de Taxus cultive in vitro", *Can. J. Bot.*, 60:1583–1589.

Fett–Neto, Arthur G., et al. (1992) "Cell Culture of Taxus as a Source of the Antineoplastic Drug Taxol and Related Taxanes", *Biotechnology*, 10:1572–1575.

Byrde, R. J. W. (1979) "Role of Polysaccharide–Degrading Enzymes in Microbial Pathogenicity", *Microbial Polysaccharides and Polysaccharases* (Chapter 18):422–424.

(1991–92) "Technical Information", *Sigma Plant Cell Culture* 49–59.

*Primary Examiner*—Irene Marx
*Attorney, Agent, or Firm*—Townsend and Townsend and Crew

[57] ABSTRACT

The present invention provides haploid cells and their derivatives which are cultured in vitro to produce taxanes and other metabolites that evolve from the isoprenoid biosynthesis pathway.

10 Claims, 3 Drawing Sheets

TAXANE PRODUCTION IN HAPLOID-DERIVED CELL CULTURES

BACKGROUND OF THE INVENTION

The present invention relates to the production and recovery of taxane compounds. In particular, it relates to cell cultures of haploid origin from *Taxus spp.* and to new methods of recovering taxanes from plant tissue.

Taxane compounds, in particular taxol, have significant antitumor activity and have been the focus of investigations to develop these compounds as drugs for the treatment of cancer. These compounds have also been shown to inhibit congenital polycystic kidney disease (Woo et al. *Nature* 368 759 (1994)). Taxol, originally isolated from the bark of the Pacific yew, *Taxus brevifolia*, was recently approved by the Food and Drug Administration for use against ovarian cancer and has also shown activity against breast, lung and other cancers.

Continued testing of taxol and other taxanes require quantities which cannot be obtained from the scarce natural source. *T. brevifolia* is a rare tree, grows slowly, and is not cultivated. In addition, thousands of pounds of bark are required to produce one pound of taxol. Moreover, extraction of the bark is complicated, and product variability occurs.

Because of the scarcity of naturally occurring taxol, numerous investigators have attempted to increase the supply of taxol and other taxanes. For instance, cell suspension cultures of sporophytic tissues have been shown to produce taxol (U.S. Pat. No. 5,019,504). In addition, recent reports describe the total synthesis of taxol (see, Holton et al. *JACS* 116:1597 (1994) and Nicolaou et al. *Nature* 367:630 (1994). These syntheses, however, involve too many steps to be commercially feasible (Flann, *Science* 263:911 (1994)).

Increased availability of taxanes will facilitate investigations to synthesize analogs of taxol or identify other taxanes with similar anti-tumor activity but having improved properties. For instance, taxol is relatively insoluble in aqueous solutions. As a result, taxol is usually dissolved in an oily base of castor oil and alcohol and administered in this form. The identification of related compounds with increased aqueous solubility could provide compounds with better cellular penetration and efficacy than is found with taxol.

Despite advances in the art, availability of taxol and other taxane compounds remains a critical limitation in further investigation and therapeutic use of these compounds. The present invention addresses these and other needs.

SUMMARY OF THE INVENTION

The present invention provides methods of producing taxanes, for example taxol, from plant tissue cultures. The methods comprise culturing haploid or haploid-derived cells from *Taxus spp.* (e.g., *Taxus brevifolia*) under conditions suitable for the production of the taxane by the cells, and recovering the taxane from the cells. The methods typically include a step of aging the cell culture before recovering the taxane.

The haploid cells are preferably from gametophytic tissue, especially the female gametophyte. The cells can be haploid, diploid, or polyploid.

In addition, the invention provides methods of recovering bound taxanes from cell cultures or other plant tissue. Bound taxanes are typically released by treating the cell culture with a glycosidase, such as xylanase.

Also provided are culture media which substantially lack nitrates. An exemplary medium is DV medium.

The invention further provides plant cell cultures comprising gametophytic cells of *Taxus spp.* The cells typically differentiate into archegonial initials (female) or sperm cells (male).

Definitions

The terms "taxanes" or "taxoids" refer to compounds comprising the tricyclic ring nucleus shown by The chemical structure of taxanes is described in Gueritte-Voegelin *J. Nat. Prod.* 50:9–18 (1987).

Taxanes of the invention can also be identified through the use of a monoclonal antibody, TA 04, which is specific for a common epitope of the tetracyclic taxane nucleus. This antibody is commercially available from the Hawaii Biotechnology Group. Taxanes can be further identified by their chromatographic behavior in a "taxane" column and their characteristic UV spectra in the 190 to 600 nm range. Taxane-like activity can be assayed using an in vitro microtubule polymerization assay as described in U.S. Pat. No. 5,019,504.

The terms "haploid cell cultures" refer to cell cultures in which each cell contains a single copy of each chromosome, as opposed to diploid or polyploid cells which contain two or more copies of each chromosome. Haploid cells of the invention are typically derived from male or female gametophytic tissue. Gametophytic tissue includes all haploid cells derived from meiosis of the megasporocyte (female gametophyte) or microsporocyte (male gametophyte).

"Haploid-derived" cells are homozygous diploid or polyploid cells which arise from haploid cells either spontaneously or by manipulation of the cultures. Such cells may comprise more than one nucleus and can arise spontaneously in culture, from fusion (spontaneous or induced) of protoplasts derived from the haploid cells, or by treatment of the cells with compounds known to increase ploidy such as colchicine.

The term "aseptic culture" refers to plant cell cultures consisting essentially of plant cells. Aseptic cultures may also include microorganisms which are added to the culture to aid in the recovery of taxanes from the plant cells. Such mixed cultures will typically comprise microorganisms (e.g., fungi, mycoplasma and bacteria) which are capable of converting plant material. For a discussion of microorganisms which attack trees and are useful in the present invention see Shigol, A. L. *A New Tree Biology* (Shigol and Associates, New Hampshire 1991). The microorganisms usually excrete one or more enzyme (e.g., glycosidases) which digest plant cell components.

The term "bound taxanes" refers to taxane compounds produced by a plant cell that are not significantly extracted by standard solvent extraction methods, but are recovered after hydrolysis of plant materials. Without wishing to be bound by any particular theory, such taxanes are thought to be covalently bound to cell wall and other components and released by, for instance, hydrolysis of the cell wall components. Hydrolysis is typically carried out by enzymatic cleavage. Other methods of releasing bound cell wall components can also be used.

A plant cell culture medium which "substantially lacks nitrates" is one in which nitrate compounds are not a significant source of nitrogen for the plant cells. One of skill will recognize that low levels of nitrates (e.g., less than about 50 mg/L of the nitrates listed in Table 2) may be included without adding a significant source of nitrogen for the plant cells.

DESCRIPTION OF THE PREFERRED EMBODIMENT

The present invention provides haploid and haploid-derived Taxus cell cultures which are suitable for the production of taxanes. It has been found that female gametophytic tissue produces significant amounts of taxanes and that cell cultures derived from this tissue are good sources of taxanes.

Any plant of the Taxus genus can produce taxanes. The haploid or haploid-derived cultures of the invention are derived from members of the genus *Taxus*, usually *T. brevifolia*, Pacific yew. The haploid tissues are female gametophytic tissue from immature seeds. The tissue is grown in nutrient media for selection of haploid cells and their derivatives as distinct from cells of the diploid sporophyte (e.g., embryo, cambium, needles, bark, roots).

The production of taxanes in haploid gametophytic cells is unexpected because the female gametophyte is normally digested as a nutrient source for the developing embryo. In the seed, taxane production would be expected to inhibit the growth of the embryo. The results provided here show that selection of gametophytic cells before they are committed to their nutritive function reverses the expected role of these cells. Such cells can be maintained in culture for a period of years. The cells are relatively insensitive to taxane production under the cultural conditions described here.

Haploid gametophytic tissue provides a number of advantages over the use of diploid sporophytic cell cultures. For instance, the use of haploid lines removes cells that have lethal genes because all alleles are expressed. Thus, cells carrying deleterious recessive somatic mutations are eliminated because they cannot divide and grow. The surviving cells are free of the "lethal gene effects" common in diploid cells of sporophytes whose reproduction involves introgression and self-fertilization. This technological clean-up removes the lethal and growth-inhibiting factors inherent in sporophytic genotypes and provides superior cell lines for the cell and tissue culture production of taxanes.

In addition, homozygous double haploids and polyploids can be developed from haploids cells by spontaneous or induced formation. Double haploids produce daughter cell products that are homozygous. These cell lines are useful for backcross studies and cell line improvement.

Haploid cell lines are also particularly useful for screening for desirable genotypes produced through mutagenesis. Mutations in genes encoding enzymes in the biosynthetic pathway can be identified more easily in haploid cells than in diploid cells. Particular genes identified in these studies can then be isolated and cloned. The cloned genes can be used to genetically engineer cultures with increased or altered taxane production.

Once a desired cell culture is established it can be easily scaled-up for growth in bioreactors and production of taxanes on a production scale. For instance, radial flow cultures can be used. Process controls in such bioreactors enable environmental, physiological and physical parameters of the culture system to be mechanized and optimized for maximum output of the desired products. For a general discussion of bioreactors and methods useful for the present invention see Shuler and *Karg Bioprocess Engineering—Basic Concepts* (Prentice-Hall, Englewood Cliffs, N.J. 1992).

To establish haploid cultures of the invention, young fruit are collected after the female gametophyte is formed. The immature fruit is preferably collected no later than several weeks after fertilization. The material is surface-sterilized according to well-known methods. Standard aseptic conditions are preferably used after cultures are established.

Isolated female gametophytes are cut to increase surface area. Gametophytes bearing embryos should be carefully identified and dissected to remove all traces of embryonic (diploid) cells so as not to inadvertently recover diploid cells. Haploid cell line recovery may be confirmed by explant location, size, staining reactions and by actually counting chromosomes in cell samples.

Haploid cells proliferate on selective media (preferably semi-solid) to produce a callus of haploid cell types and their derivatives. Since all recessive genes are expressed, many gametophytic cells may die if they contain lethal genes. The surviving cells grow into a white callus that ages and browns if subculture schedules are not maintained. The best subculture rates for scale-up are at least weekly. Once established, the haploid callus may be grown as a cell culture with cells being immobilized in a bioreactor or as a cell suspension culture using many of the available bioreactor designs.

For the recovery and scale-up of haploid cells, a medium which substantially lacks nitrates is preferably used. It is understood that modifications can be made in these media, such as substitutions of salts, e.g., addition or deletion of various components or alteration of proportions. For example, increased nitrogen (in the form of urea or arginine) increases the growth rate. Thus it is apparent that determination of suitable and optimal media for particular cells would be within the ability of a person skilled in the art.

The culture media used in the methods of the invention may be solid, semi-solid or liquid. Any gelling agent (e.g., agar, Gelrite and the like) commonly used to solidify media can be used. For establishment of cell suspension cultures, an inoculation density of about 1 gm per 100 ml medium is preferably used. Cells are subcultured every 10 to 14 days or sooner to scale-up for cell mass.

For taxane production, cells should be aged for at least about 3 weeks. As the term is used here, "aging" and senescence are distinguished from maturation. Aging is a consequence of external events that accumulate over time, and senescence represents an endogenously controlled degenerative program leading to cell death, whereas maturation, as in the conversion of archegonial cells to oocytes, represents a genetically determined developmental plan.

Aging and senescence were achieved by withholding nutrients and subculture routines. Withholding of subculture leads to a slow browning of cells and to the leakage of metabolites into the culture medium. Aged and senescent cultures contained both live and dead cells, even after 1 yr. without subculture, as assessed by direct microscopic observations with Evan's blue and fluorescein diacetate.

During the aging process, cells released membranes and particles by sloughing off from cell walls into the culture medium. These materials reacted weakly with cytochemical stains (Feulgen-Giemsa, Stains-all). Some of these membranes and particles also reacted with the antibody for taxanes.

Culture conditions are optimized for the steady-state production of taxanes. Culture conditions typically include low light conditions, preferably darkness, to maintain heterotrophic growth and preserve the development and integrity of haploid cells. Temperature, air pressures and gaseous atmospheres can be varied as necessary to approximate conditions found in the seed.

Taxanes may be recovered according to standard techniques, for example, as described in U.S. Pat. No. 5,019,504. Adsorbent beads may be used to remove the taxanes produced. In addition, particulate matter released by the cells may be used to adsorb the taxanes. The particular adsorbent material is not a critical aspect of the invention, so long as the material provides a sink for removing the end-product from the reaction sequence.

Although not essential, taxane production can be induced by the addition of various elicitors. Such compounds include fungal elicitors, vanadyl sulfate, 3,4-dichlorophenoxy triethyl(amine), and the like which generally stimulate production of secondary products in plant cells.

In addition to haploid-derived cell cultures, the present invention also provides new methods of recovering taxanes. As described below, taxanes have been localized in cells even after the tissue has been extracted with methanol. Taxanes have been located on the exterior cell wall surface of female gametophytic tissues, particle surfaces and cell wall fragments of enzymatically digested cells, colloidal film surfaces, the cell wall plus interstitial space of adjacent cells, the wounded surfaces of freshly harvested twigs, particles coating the exterior of cell walls and sheets of cell debris.

Additionally, enzyme treatment of exhaustively extracted tissues yields taxanes that are detectable by HPLC. By contrast, the nonenzymatically treated controls do not yield free or bound taxanes. The extraction methods of the invention allow recovery of these bound materials.

The bound compounds left behind by standard extraction methods provide an extended pool that increases the diversity of known taxanes and their precursors. This diversity is a source for potentially new and novel antitumor compounds and/or their synthons. The enzymatically released compounds show an enhanced solubility in polar solvents. Enhanced solubility in polar solvents, in particular aqueous solutions, provides better cellular penetration and efficacy than is found in the relatively insoluble taxol.

Additionally, enzymatic treatment of taxane productive sources provides digestion products that are useful as catalytic surfaces and elicitors of further taxane production. With digested walls of cells and tissues, the resultant protoplasts are a source of genetically alterable cells that enable the design of genetically superior lines and potentially taxane productive plant products.

The recovery methods of the invention typically use enzymatic cleavage to release bound taxanes. Exemplary enzymes for this use include glycosidases such as pectinase, xylanase, cellulase and the like. Such enzymes are commonly used to digest cell wall components for the production of protoplasts. Other degradative enzymes known to those of skill in the art, such as lignases, chitinases and the like, can also be used. Other compounds or conditions suitable for the cleavage of chemical bonds in the cell wall or other components of the cell can also be used for this purpose. Suitable methods include the use of strongly oxidizing conditions, acid or alkaline hydrolysis (using either mild or harsh conditions) and the like. Alternatively irradiation or heat can be used to release the compounds.

The methods used to release bound taxanes may in some cases result in artifactual alteration of the chemical structure of the purified taxanes (see, e.g., Miller *J. Nat. Prod.* 43:425 (1980)). Such alterations can be useful as a source for taxanes with improved properties, such as solubility, activity and the like. These compounds can also be used as synthons for the synthesis of new taxanes.

Enzymes (e.g. cellulase, pectinase and xylanase) as reagents in "live" cultural conditions, whether continuous or batch, can remove bound taxanes and related alkaloids. The released taxanes can then be isolated by extraction. The enzymatic release of other potential substrates into the culture medium would affect synthesis with a positive or negative effect on total yield. Hence, enzymes can be used for process control (feedforward or feedback) of taxane and related alkaloid production. This can be used to manipulate the culture environment to optimize for rapid growth or maximum yield of desired compounds.

The following examples are intended only to further illustrate the invention and not intended to limit the scope of the invention which is defined in the attached claims.

EXAMPLE 1

Establishment of Haploid cultures

Callus cultures

Plant material of *Taxus brevifolia* and *T. canadensis* was collected from an arboretum and several forest sources. When necessary, it was stored at 4° C. until processed. The plant material consisted of leaves, buds, new and old shoot segments (3 to 5 year old) and excised embryos from immature and ripe seeds. These represent the diploid (sporophytic) cells. All tissues were surface-sterilized as indicated in Table 1.

TABLE 1

*Taxus Brevifolia* Tissue Culture
Samples of fruit were freshly collected from a specimen of
*Taxus brevifolia* and processed immediately. Washing and surface
sterilization were conducted as follows:

TISSUES WASHED IN
ABOUT 5% LINBRO AND
WATER FOR SEVERAL MINUTES
|
THOROUGHLY RINSED IN
SEVERAL CHANGES OF
DISTILLED WATER
|
STERILIZED WITH 30%

TABLE 1-continued

*Taxus Brevifolia* Tissue Culture
Samples of fruit were freshly collected from a specimen of
*Taxus brevifolia* and processed immediately. Washing and surface
sterilization were conducted as follows:

SOLUTION OF HYDROGEN
PEROXIDE (30% OF
ORIGINAL CONCENTRATION)
FOR ABOUT 15 MINUTES
|
RINSED WITH STERILE DISTILLED
WATER 2–3 TIMES.
|
TRANSFER MATERIAL TO STERILE
CONTAINER.
|
STERILIZE WITH 10%
OF CHLOROX BLEACH FOR ABOUT
15 MINUTES.
|
RINSED WITH STERILE DISTILLED
WATER 2–3 TIMES.
|
RINSED FOR ABOUT AN HOUR
STERILE 1% SOLUTION OF ASCORBIC
ACID ADJUSTED TO pH 7.0.
|
RINSED WITH STERILE DISTILLED
WATER 2–3 TIMES.
|
FOLLOWING THE STERILIZATION
PROTOCOL, THE SAMPLES WERE
ASEPTICALLY DISSECTED AND
PREPARED FOR INOCULATION
ONTO SOLID CULTURE MEDIA.

All procedures used aseptic techniques. The fruit was dissected into two parts: fruit flesh and seed. The seed was cut in half and the female gametophyte was removed and placed on solid TMH and/or DV medium. The two halves of the gametophyte were placed so their cut surfaces contacted the media. The samples were incubated at 23° C. in the dark. No antimicrobial agents were used. Callus appeared at the cut edges of tissues 2 weeks later and cells were removed with a scalpel and forceps. Non-browning callus was selected and subcultured every week for scale-up and every 3 weeks for maintenance.

Of all the explant sources only the haploid cell lines survived on the TMH or DV media (Table 2). All other cell lines (diploid) eventually browned and died.

One of skill will recognize that the components of these media may be varied in a number of ways without significantly affecting growth of the cells. For instance, the plant growth regulators of the TMH medium may be used in place of those identified for DV, and vice versa. The components for each medium listed in Table 2 may also be supplemented with cyclodextrins (1 mg/L to 1 g/L). Cyclodextrins are useful in increasing solubility of insoluble components. In addition, cyclodextrin concentration can be used to adjust the osmolality of the medium to maintain proper turgor pressure in the cells.

Cell lines were maintained on semi-solid medium with subcultures every 3 weeks. Before initiation of new subcultures, cells were regularly checked karyotypically and with an antibody probe for taxane production. Each cell typically showed at least 0.5 ng/ml of taxol, 0.5 ng/ml cephalomannine and/or 17 ng/ml of baccatin 3.

TABLE 2

MEDIA COMPOSITION CHART
Media for the Propagation of *Taxus brevifolia* (in mg/liter)

|  | TMH | DV |  | TMH | DV |
|---|---|---|---|---|---|
| Nitrates |  |  | Vitamins |  |  |
| $NH_4NO_3$ | 400 | 0 | THIAMINE-HCL | 0.7 | 2.0 |
| $Ca(NO_3)_2 \cdot 4H_2O$ | 370 | 0 | NICOTINIC ACID | 0.05 | 1.0 |
| $KNO_3$ | 340 | 0 | PYRIDOXINE-HCL | 0.05 | 0.5 |
|  |  |  | GLYCINE | 0.2 | 20 |
|  |  |  | CA PANTOTHENATE | 0 | 1.0 |
|  |  |  | FOLIC ACID | 0 | 1.0 |
| Sulfates |  |  | Other Organics |  |  |
| $MgSO_4 \cdot 7H_2O$ | 556 | 0 | SUCROSE | 30000 | 20000 |
| $MnSO_4 \cdot 7H_2O$ | 2.23 | 2.0 | INOSITOL | 200 | 1000 |
| $ZnSO_4 \cdot 7H_2O$ | 0.86 | 3.0 | CASEIN HYDROLYSATE[1] | 500 | 300 |
| $CuSO_4 \cdot 5H_2O$ | 0.25 | 0.01 | L-GLUTAMINE | 450 | 400 |
| $Na_2SeO_3$ | 0 | 0.01 | L-ARGININE | 200 | 0 |
|  |  |  | K CITRATE | 0 | 100 |
|  |  |  | ASCORBIC ACID | 0 | 50 |
|  |  |  | GLUCOSAMINE HCL | 0 | 10 |
|  |  |  | TRYPTOPHAN HCL | 0 | 1 |
|  |  |  | L-ASPARAGINE | 0 | 100 |
|  |  |  | GLUTATHIONE | 0 | 10 |
|  |  |  | L-SERINE | 0 | 50 |
|  |  |  | L-THREONINE | 0 | 50 |
|  |  |  | L-TYROSINE | 0 | 50 |
|  |  |  | L-LYSINE | 0 | 10 |
|  |  |  | L-CYSTEINE | 0 | 1 |
| Halides |  |  | Growth Regulators |  |  |
| $CoCl_2 \cdot 6H_2O$ | 0 | 0.01 |  |  |  |
| $CaCl \cdot 2H_2O$ | 110 | 0 | BAP | 0.5 | 0.5 |
| $NiCl_2$ | 0.025 | 0.01 | NAA | 2.0 | 2.0 |
| KI | 0 | 0.1 |  | OR |  |
|  |  |  | 2,4-D | 0 | 3 |

TABLE 2-continued

MEDIA COMPOSITION CHART
Media for the Propagation of *Taxus brevifolia* (in mg/liter)

| | TMH | DV | | TMH | DV |
|---|---|---|---|---|---|
| Phosphate, Borate, Molybdate | | | Media Solidification | | |
| KH$_2$PO$_4$ | 170 | 200 | GELRITE | 3000 | 3000 |
| H$_3$BO$_3$ | 0.62 | 0.3 | (not used for cell | | |
| Na$_2$MoO$_4$ | 0.25 | 0 | suspension media) | | |
| Iron | | | Hydrogen Ion Concentration | | |
| FeSO$_4$-7H$_2$O | 27 | 6.95 | pH | 5.8 | 5.8 |
| Na$_2$EDTA-2H$_2$O | 37.3 | 9.3 | | | |

The DV medium also contains (in mg/L) urea, 200; Mg glycerophosphate, 100; Mg orotate 400; Ca glycerophosphate, 20; N-carbamylaspartate, 10; putrescine HCL, 1.0; spermidine phosphate, 1.0; and γ-amino-n-butyric acid, 10.
[1]Casein Hydrolysate specification: Sigma Hy-Case SF from bovine milk (low sodium).

Cell suspension cultures

Callus was introduced into cell suspension culture using 1 liter nippled flasks rotating at 1 rpm in darkness at 22° to 24° C. Each flask contained 200 ml of liquid medium (TMH) and was inoculated with ca 1.5 gm of packed-cell-volume (PCV). After 2 to 3 weeks, cell suspensions were filtered through a 250 µ polyester screen to remove large unfragmented cell clusters and a new PCV developed to inoculate and grow more uniform and synchronized cell suspensions.

Subculture of the nipple flask cultures was done at 2 week intervals by filtering the cells from the used media with a 20 µ polyester screen. 200 ml of fresh TMH was used as a replacement. The cultures were split in half at subculture time. Enough cells were removed at each subculture to adjust the concentration of cells so that it remained approximately constant. Cells can be maintained indefinitely by this procedure and the most rapid doubling rate is usually about 9 days. While growth rates vary with the initial concentration of plant growth regulators (PGRs), very low levels of PGRs have been required to obtain good culture growth.

Cells were harvested from suspension cultures and probed with a taxane-specific antibody to localize taxanes within cells, on their surface, and in small cell clumps. These were compared with the taxane production in the mother 30 yr old tree (i.e. from stems of the tree from which seeds and haploid cells were derived) as described below.

Results

Cells from immature female gametophytes initially represented a mixture of two basic transitional ontogenic types: a) small (<100 µm diameter) cells destined to serve as the female gametophyte in the seed and b) large multi-nucleate (>250 µm diameter) cells that normally serve as archegonial initials. In situ, oocytes are derived from archegonial cells of the female gametophyte. Upon explanting tissues of the gametophyte to the medium, the archegonial initials proliferated and were released onto the culture plates as large individual cells. The ontogenetic program of these cells was characterized by free nuclear stages and is consistent with archegonial development as previously reported for *Taxus*.

In *Taxus cuspidata*, oocytes are reported as being of multiple origin in the gametophyte and derive from haploid archegonia, this phenomenon has not been captured previously by cell and tissue methods. A striking feature of cultured cells from the female gametophyte that are programmed to become archegonia and eggs is their propensity to vary their cell cycle so that free nuclei were produced just as in nature. One advantage of such cells is that their multiple free-nuclear states may substitute for expressions of ploidy to enhance the robustness of the genotype. If genes for biosynthetic capacity are expressed by all nuclei, their additive expression should contribute to enhanced biosynthetic capacity.

Small haploid cells in gametophytes from ripe seeds normally provide nourishment for the embryo as the seed matures. When in suspension culture, these cell types did not produce freely soluble taxanes in the culture medium. Somehow gene expression was repressed. De novo production of bound taxanes had to be elicited. The consumption of nutrients created by the lack of subculture and the release of metabolites during aging may have stimulated and supported the growth of multinucleate cells. It is known that the degeneration of cells during megasporogenesis stimulates somatic cells to differentiate as embryo sacs. However, it is now clear that the presence of an organized and differentiated group of cells such as is found in nodules or spheroblasts is not needed for taxane biosynthesis by haploid-derived cells.

Cells with more than one haploid nucleus and/or that spontaneously doubled were always over 100 µm in diameter. Karyological studies using Feulgen/Giemsa and DAPI staining to compare haploid cells to diploid cells from root tips and sporophytic callus usually showed smaller nuclear volumes in eight fresh and fixed preparations. The number of chromosomes was determined by counts as n=12 and 2n=24. The double haploids and polyploids (1% population) seemed to be of spontaneous origin.

On semisolid media, the doubling rate of fresh callus at 23° C. on TMH was not greater than 25 days, as calculated by weighing the calli. In suspension cultures, cell populations with doubling rates of 8 or 9 days were selected. During the recovery of oocyte-like cells on DV medium, the multiplication of cells was initially rapid, with a doubling rate of 3 to 4 days for the first 2 to 3 wk; the doubling rate then stabilized at 7 to 10 days.

A variety of conifer culture media, e.g., ½LP (von Arnold et al. *Can. J. Bot.* 59:870–874 (1981)), DMH (Hong et al. in *Woody Plant biotechnology* pp 105–121 (Plenum Publishing New York, 1991)), and WPM for broad-leaves trees (Lloyd et al. *Proc. Plant Propogators Soc.* 30:421–427 (1980)), were used without the success evident for TMH and DV. Some sporophytic lines (needles, current year stem sections) grew best without plant growth regulators, but over the long run, the slow growth on TMH was especially suitable for maintaining cultures on a biweekly culture regimen over several years.

The DV medium was formulated to replace nitrates with organic N sources, reduce sulfate levels, and provide a more chemically reductive environment at pH 5.8 and 23° C.

Figure 1A:
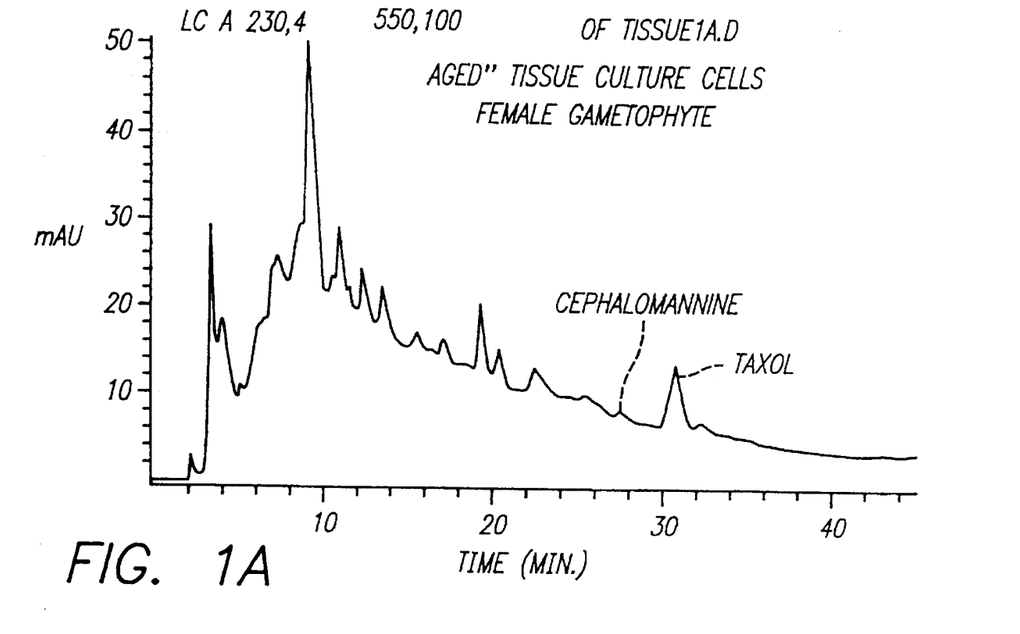
FIGS. 1A and 1B are chromatograms of aged (1A) and non-aged (1B) tissue culture cells of the invention. Taxanes are identified by spectral properties and elution time as compared to taxane standards. No free taxanes were detectable in the non-aged cells.
Figure 1B:
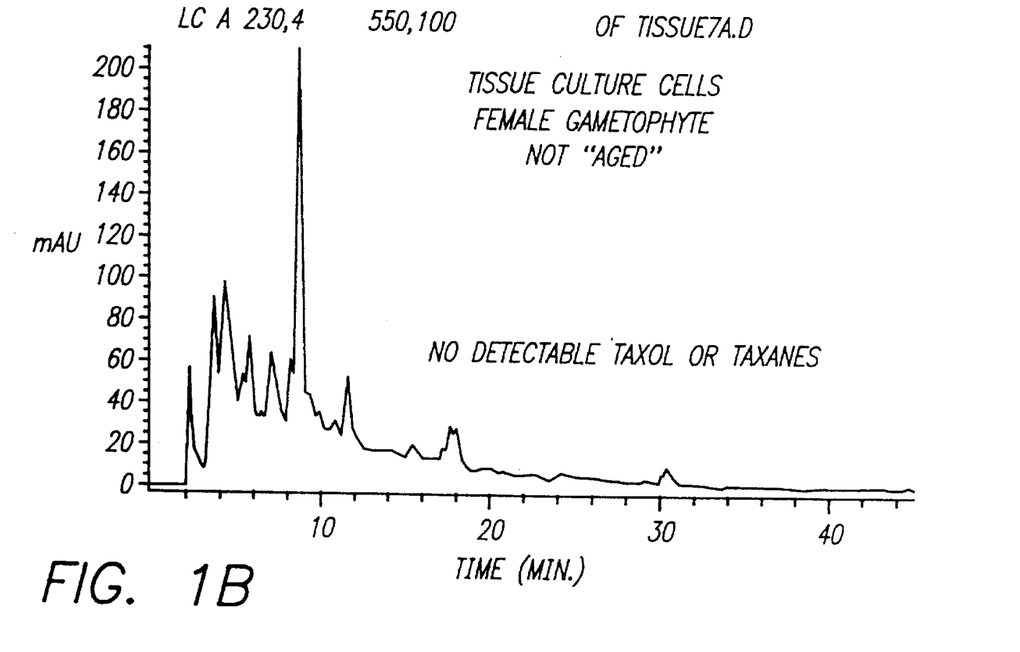

Cultures that were physiologically "aged" i.e., without subculture for periods greater than 2 mo., contained methanol-extractable free taxanes with characteristic UV spectra, detectable by HPLC, whereas non-aged cells did not (FIGS. 1A and 1B).

EXAMPLE 2

Localization of taxanes in sporophytic tissue

A freshly cut branch, of a 30-year-old female mother tree of *Taxus brevifolia*, about 0.75 cm in diameter, representing several years of growth and known to contain taxanes, was sectioned without fixation. The branch was cut to a length of approximately 1.5 cm and mounted fresh. Ten micron longitudinal sections were rinsed with tris buffered saline (TBS), pH 7.0. The sections were treated with anti-taxane antibodies (TA04) or plain buffer. This was followed with three rinses in the TBS. Fluorescein isothiocyanate (FITC) labeled antibody or plain buffer was used for the secondary treatment. A final three rinses with buffer were used to finish the protocol.

Additionally, similar sample tissues were tested for taxane content using a gold labeled secondary antibody to replace the FITC labeled secondary previously used. This protocol confirmed observations that localized the taxanes in the area between the branch's bark and woody center.

All treatments localized taxanes in and around cell wall structures. Of particular interest is the intense and localized distribution of taxanes detected at the cut end of the branch segment. This indicates the influence of wounding in taxane production. In turn, the wounding reactions implicate the participation of oxidative bursts in the stimulation of taxane production.

Localization of taxanes in female gametophytic tissue

Fresh (unfixed) female gametophytic tissue from a recently harvested seed was treated as described above with anti-taxane polyclonal antibodies and FITC labeled secondary antibodies.

Taxanes were detected on the exterior surface of the gametophytic cells. In particular, the reactive sites appeared as distinct points on the cell wall surface as well as distinct particles free of the cell wall. This indicates that taxanes exist as entities bound to insoluble materials occurring on the surfaces of cells. The detection of free taxane positive particles indicates that they are releasable as discrete materials.

Localization of taxanes in haploid cell cultures

Fresh (unfixed) female gametophytic tissue from an established and cultivated tissue culture line (subcultured at regular intervals, usually 10 days to 2 weeks, and maintained in constant darkness at 20° C.) was also tested for taxanes as described above. Taxane positive sites were detected on the exterior of cell walls. Detached taxane positive particles were also detected.

HPLC analysis of methanol extracted tissue culture samples showed no detectable taxanes. However, cultures that were physiologically "aged" through nutritional stress contained methanol extractable taxanes detectable by HPLC. Localization of taxanes in fixed gametophytic tissue The female gametophytic tissue of a freshly harvested seed was fixed in 4% v/v glutaraldehyde at pH 7.0. Sample sizes ranged from about 1.5 to 3.5 mm cubed. The tissue was dehydrated with an 80 to 100% v/v ethanol series. The ethanol also acted to extract any freely soluble taxanes in the tissue samples. Sections affixed to glass slides were treated with antibodies for the detection of taxanes as described above. Taxanes were located in the interstitial space between adjoining cells and along various cell wall surfaces including those making up the exterior of the sample.

EXAMPLE 3

Free taxane content of Taxus tissues and haploid cultures

In separate HPLC analyses, tissues of the 30-yr.-old mother tree used as a source for the cultures described here were shown to contain free taxanes. Free taxanes produced in air-dried samples of shoots and bark from the mother tree were 0.002% (taxol), 0.003% (cephalomannine), and 0.002% (baccatin-III), all within ±0.0001%. This is equivalent to about 20 mg of each compound per kg of tissue.

Early subcultures of the female gametophyte and haploid derivatives obtained from seeds showed undetectable or trace levels of free taxanes. The haploid cell cultures starved on either culture medium (Table 2) yielded 270 µg free taxol per kg FW. Free taxol in the culture medium was recovered at 350 µg/kg of cells. This gave a total recovery of 620 µg of free taxol per kg of aged cells or ca 3% of that obtained from the mother tree on an equivalent weight basis.

To extract taxanes, samples were extracted in 100% methanol three times. The combined extracts were concentrated and mixed with a minimum of 2 volumes of water and partitioned against methylene chloride twice. The methylene chloride was evaporated to dryness and the resulting residue was dissolved in a known volume of 100% methanol and subsequently diluted to 66% with water. This preparation was thoroughly mixed and passed through a 0.22 µm nylon filter before HPLC.

Detection of Taxanes in Enzyme-treated Tissues

Samples of *Taxus brevifolia* wood, bark, needles (diploid sources) and female gametophytic tissue cultures (haploid and double haploid sources) were each treated with the enzymes cellulase, pectinase, and xylanase for an appropriate amount of time and in appropriate conditions. The resultant mixture was appropriately extracted with methanol and analyzed with high pressure liquid chromatography for soluble taxanes.

Figure 2A:
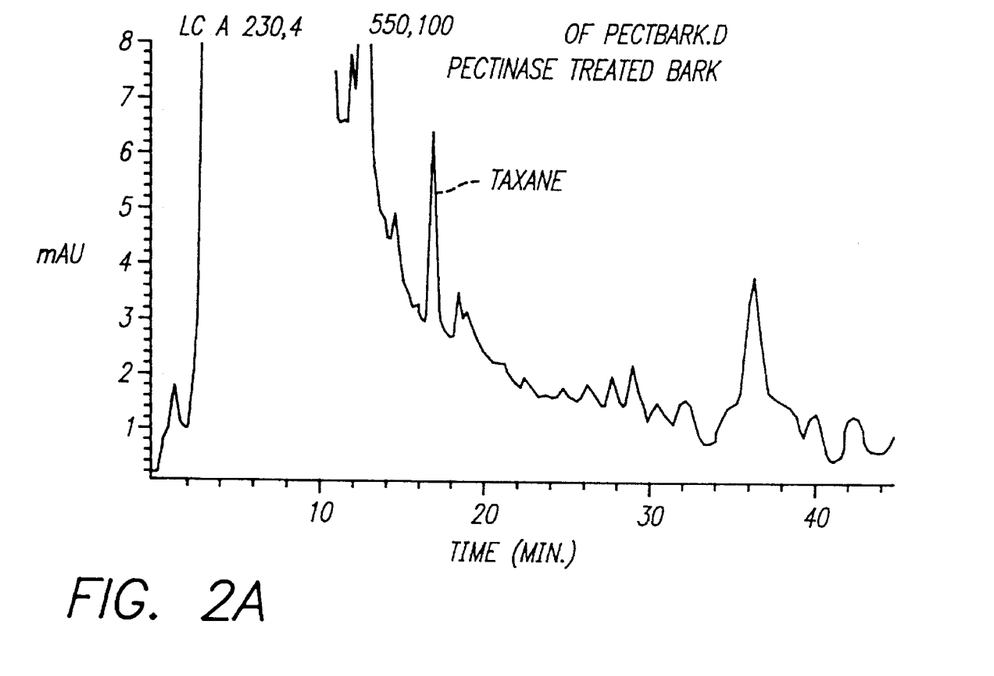
FIGS. 2A and 2B are chromatograms from pectinase treated bark (2A) and control bark tissue (2B) which was not treated with the enzyme.
Figure 2B:
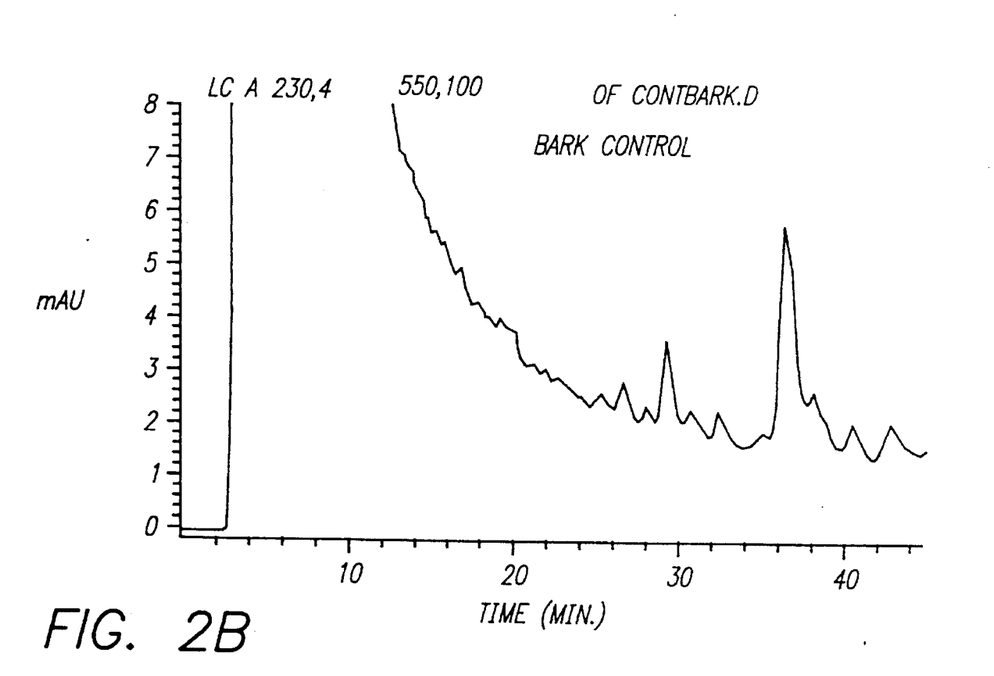

All enzyme treated samples showed a number of compounds not detectable in any of the controls. For instance, pectinase treated bark sample showed a clearly identifiable taxane peak not found in the control (FIGS. 2A and 2B).

To confirm that taxanes were released by enzymatic cleavage, samples (wood, bark, needles and tissue culture) were first extracted with methanol and analyzed by HPLC to confirm taxane content. Next, the tissues were extracted at least 7 to 8 more times to remove taxanes to a nil level. An additional analysis by HPLC was performed to confirm the removal of soluble taxanes. After extraction, the tissues were rinsed in double distilled water (3x) to remove the methanol. The enzymes (cellulase, pectinase and xylanase) and ground tissues were paired and mixed with 0.05 molar citrate buffer at pH 5.0 to give 76.8 units per gram fresh weight of tissue (U/gFW) for cellulase, 0.52 U/gFW for pectinase and 128.8 U/gFW for xylanase. Enzyme mixtures were incubated at 35° C. for 27 hours and subsequently extracted with methanol to recover bound taxanes released by the enzyme treatment.

Methanol extracts of enzyme (cellulase, pectinase and xylanase) treated bark and a control (no enzyme treatment) were tested for their total taxane content with a competitive inhibition enzyme immunoassay (CIEIA) using the anti-taxane antibody TA04 (Hawaii Biotechnolgy Group). The antibody is specific for a common epitope of the tetracyclic taxane nucleus and is known to be capable of detecting at least the following compounds:

| | Taxane | IC$_{50}$ nanomolar |
|---|---|---|
| 1. | taxol | 7 |
| 2. | 10-deacetyltaxol | 10 |
| 3. | 7-epi-10-deacetyltaxol | 15 |
| 4. | 7-xylosyl-10-deacetyltaxol | 17 |
| 5. | cephalomannine | 8 |
| 6. | baccatin III | 12 |
| 7. | baccatin V | 10 |
| 8. | 10-deacetylbaccatin III | 21 |
| 9. | 7-epi-10-deacetylbaccatin III | 27 |

Note: IC$_{50}$ = The concentration of analyte required for 50% inhibition of binding of the antibody to the solid phase antigen.

After all free taxanes were removed by the methanol extraction of haploid cell cultures and a wood sample from the same tree, each residue was partially hydrolyzed with one of the following enzymes: pectinase, hemicellulose, cellulase, or xylanase. Of all these treatments, only the xylanase released UV-absorbing compounds. Recovery and detection of taxane reactivity was based on a CIEIA procedure. The yield of bound compounds was 11 μg/kg of extracted cells (air-dried, aged for 2.5 months). This compared with 300 μg/kg of bound taxanes recovered from wood (no bark) of the mother tree.

When samples of bark from the mother tree were treated with the same enzymes, under identical conditions, bound taxanes could not be detected in a repeatable fashion. In one positive result, an unidentified taxane-like compound was released by the pectinase treatment.

Figure 3A:
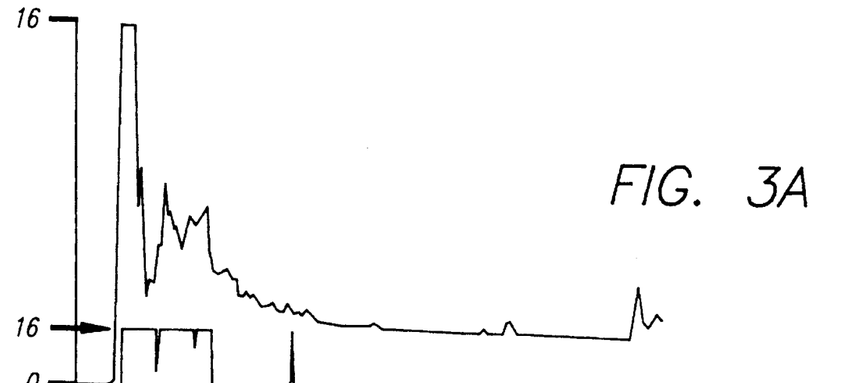
FIGS. 3A, 3B, and 3C are chromatograms as follows: methanol extracted aged cells of the invention (3A), xylanase treated aged cells (3B), and standards showing the location of peaks for known taxanes (3C) In FIG. 3C, the numbered peaks are as follows: 1,10-deacetylbaccatin III; 2, baccatin III; 3,7-epi-10-deacetylbaccatin III; 4,10-deacetyltaxol; 5, cephalomannine; 6, taxol; 7,7-epi-10-deacetyltaxol.
Figures 3B, 3C:
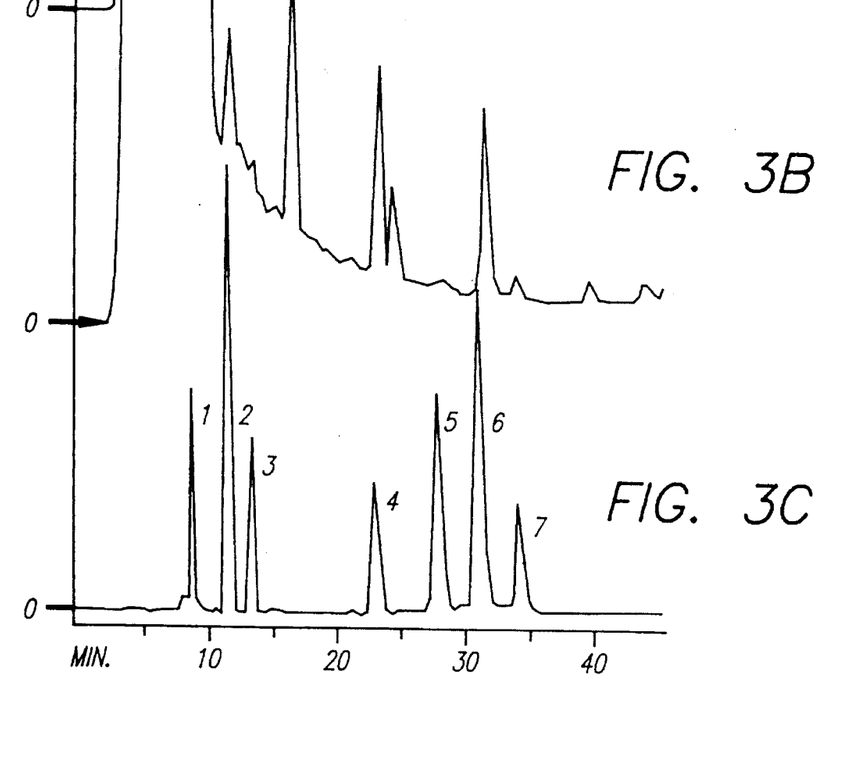

The HPLC analyses showed that compared to controls (FIG. 3A), the xylanase treatment released a number of compounds (FIG. 3B) that corresponded in chromatographic behavior to chemical standards (FIG. 3C). However, the UV spectra of the released compounds were not characteristic of the standards. Yet, as a group of taxanes bearing the taxane ring, they reacted with the TA04 antibody. If all of the UV-absorbing compounds released by the xylanase treatment indeed bear the taxane ring, the total yield of released compounds estimated by HPLC analysis was 5 to 6 mg/kg of residue from aged and extracted haploid cell suspensions.

Our results show that bound compounds having an immunocyto-chemical reaction to the taxane ring are associated with the cell wall and its extracellular membranes. We show that the antibody-reactive compounds are covalently bound to cells and can be released into the culture medium by a xylanase treatment of residues previously extracted to remove the free taxanes. β-Xylose derivatives of the hydroxyl group at carbon 7 of the taxane ring in compounds having an oxetane ring have been reported.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. A method of producing a taxane, the method comprising:

establishing a cell culture from archegonial cells, oocytes or a combination thereof from Taxus spp.;

culturing the cell culture in a medium which comprises less than about 50 mg/L nitrate under conditions suitable for the production of the taxane;

nutritionally stressing the cell culture by withholding nutrients and subculture routines; and recovering the taxane from the cell culture.

2. The method of claim 1, wherein the cells are from *Taxus brevifolia*.

3. The method of claim 1, wherein the medium is DV medium, as shown in Table 2.

4. The method of claim 1, wherein the taxane is taxol.

5. The method of claim 1, wherein the step of recovering the taxane includes releasing bound taxane with a glycosidase.

6. The method of claim 1, wherein the glycosidase is xylanase.

7. A method of extracting bound, insoluble taxanes from a Taxus spp. cell, the method comprising treating the cells with a hydrolytically effective amount of at least one glycosidase to release the bound, insoluble taxanes; and recovering the taxanes.

8. The method of claim 7, wherein the glycosidase is xylanase.

9. The method of claim 7, wherein the cell is from *Taxus brevifolia*.

10. The method of claim 7, wherein the cell is from a cell culture.

* * * * *

UNITED STATES PATENT AND TRADEMARK OFFICE
CERTIFICATE OF CORRECTION

PATENT NO. : 5,547,866
DATED : August 20, 1996
INVENTOR(S) : Don J. Durzan et al.

It is certified that error appears in the above-identified patent and that said Letters Patent is hereby corrected as shown below:

Column 1,
Line 11, kindly insert
-- This invention was made with Government support under Grant No. NAG9-285, awarded by the National Aeronautics and Space Administration. The Government has certain rights in this invention. --

Signed and Sealed this

Twenty-first Day of June, 2005

JON W. DUDAS
*Director of the United States Patent and Trademark Office*